(12) United States Patent
Jean

(10) Patent No.: US 11,454,571 B2
(45) Date of Patent: Sep. 27, 2022

(54) SAMPLING TOOL FOR LUBRICATING FLUID ANALYSIS

(71) Applicant: PRATT & WHITNEY CANADA CORP., Longueuil (CA)

(72) Inventor: Maurice Jean, Morin-Height (CA)

(73) Assignee: PRATT & WHITNEY CANADA CORP., Longueuil (CA)

(*) Notice: Subject to any disclaimer, the term of this patent is extended or adjusted under 35 U.S.C. 154(b) by 309 days.

(21) Appl. No.: 16/546,654

(22) Filed: Aug. 21, 2019

(65) Prior Publication Data
US 2021/0055185 A1    Feb. 25, 2021

(51) Int. Cl.
| | |
|---|---|
| G01N 1/14 | (2006.01) |
| G01M 15/14 | (2006.01) |
| G01N 1/40 | (2006.01) |
| G01N 33/28 | (2006.01) |

(52) U.S. Cl.
CPC .............. *G01N 1/14* (2013.01); *G01M 15/14* (2013.01); *G01N 1/4077* (2013.01); *G01N 33/2888* (2013.01); *G01N 2001/4088* (2013.01)

(58) Field of Classification Search
CPC ........... G01N 1/2035; G01N 2001/205; G01N 2001/2071; G01N 33/2858; G01N 15/0272; G01N 33/28; G01N 1/10; G01N 1/2202; G01N 1/2205
See application file for complete search history.

(56) References Cited

U.S. PATENT DOCUMENTS

| | | | | |
|---|---|---|---|---|
| 1,753,394 A | * | 4/1930 | Watson | F16J 13/04 220/322 |
| 2,447,595 A | * | 8/1948 | Pigott | G01N 1/2035 73/863.58 |
| 3,068,442 A | * | 12/1962 | Kubik | H01R 13/447 439/136 |
| 3,242,739 A | * | 3/1966 | Botkin | G01N 1/2035 73/863.57 |
| 3,400,575 A | * | 9/1968 | Madden | G01N 1/2202 73/61.72 |
| 3,681,562 A | * | 8/1972 | Winzen | B01D 29/05 210/94 |

(Continued)

FOREIGN PATENT DOCUMENTS

| | | |
|---|---|---|
| WO | 02087726 A1 | 11/2002 |
| WO | WO-2010085489 A1 * 7/2010 | .............. F16N 13/04 |

OTHER PUBLICATIONS

European Patent Office, Communication including the extended European search report re: patent application No. 20191917.2 dated Jan. 13, 2021.

(Continued)

*Primary Examiner* — David A. Rogers
(74) *Attorney, Agent, or Firm* — Norton Rose Fulbright Canada LLP

(57) ABSTRACT

A method and a sampling tool for collecting particles from lubrication fluid of an engine are disclosed. The particles collected may be used to conduct analysis to diagnose a condition of the engine. The tool can be detachably connectable to a lubrication system of the engine. The tool comprises an inlet for receiving lubrication fluid from the lubrication system of the engine, a filter and a pump configured to induce a flow of the lubrication fluid through the filter.

19 Claims, 9 Drawing Sheets

(56) References Cited

U.S. PATENT DOCUMENTS

| | | | | |
|---|---|---|---|---|
| 3,981,584 | A * | 9/1976 | Guymer | F01M 11/10 356/70 |
| 4,612,815 | A * | 9/1986 | Green | G01N 1/14 73/864.11 |
| 4,640,466 | A * | 2/1987 | Fishgal | B01D 19/0057 241/39 |
| 4,640,564 | A * | 2/1987 | Hill | H01R 13/447 439/137 |
| 4,930,360 | A * | 6/1990 | Tan | C23F 1/36 73/864.34 |
| 4,944,178 | A * | 7/1990 | Inoue | G01N 25/14 73/19.1 |
| 5,237,878 | A * | 8/1993 | Hackenberg | G01N 1/14 73/861.34 |
| 5,262,732 | A * | 11/1993 | Dickert | G01N 33/2888 324/204 |
| 5,289,900 | A * | 3/1994 | Aho, Jr. | F01M 11/04 137/577 |
| 5,437,199 | A * | 8/1995 | Kaplan | B63C 11/18 73/863.23 |
| 5,442,969 | A * | 8/1995 | Troutner | G01N 1/2035 73/863.71 |
| 5,485,881 | A * | 1/1996 | Toon | E21B 34/12 166/165 |
| 5,788,858 | A * | 8/1998 | Acernese | B01D 61/04 210/202 |
| 6,065,488 | A * | 5/2000 | Garcia | G01N 1/08 137/317 |
| 6,223,590 | B1 * | 5/2001 | O'Dwyer | G01N 1/40 73/61.56 |
| 6,361,687 | B1 * | 3/2002 | Ford | G01N 30/6039 210/198.2 |
| 6,391,096 | B1 * | 5/2002 | Waters | B01D 19/0031 73/19.02 |
| 6,568,342 | B2 * | 5/2003 | Mielke | B63B 5/06 114/202 |
| 6,643,570 | B2 * | 11/2003 | Bangert | G06Q 10/06 701/32.1 |
| 7,757,815 | B2 | 7/2010 | Craig | |
| 7,938,029 | B2 | 5/2011 | Campbell et al. | |
| 8,442,775 | B2 * | 5/2013 | Santos | G01N 33/2841 702/24 |
| 8,578,796 | B2 * | 11/2013 | Cho | G01N 1/24 73/863.11 |
| 8,701,506 | B2 * | 4/2014 | Morris | G01N 1/2035 73/863.86 |
| 9,476,808 | B2 * | 10/2016 | Miyashita | C12M 41/36 |
| 9,696,243 | B2 | 7/2017 | Lopez et al. | |
| 9,897,582 | B2 | 2/2018 | Jean et al. | |
| 9,976,770 | B2 * | 5/2018 | Cherry, Sr. | F24F 11/30 |
| 10,031,090 | B2 * | 7/2018 | Briden | G01T 3/001 |
| 10,330,664 | B2 * | 6/2019 | Jean | H01J 37/28 |
| 10,408,714 | B2 * | 9/2019 | Vethe | F16L 41/021 |
| 10,725,009 | B2 * | 7/2020 | Gotz | A47J 37/1271 |
| 10,732,190 | B2 * | 8/2020 | Jean | G01N 31/22 |
| 2001/0025595 | A1 * | 10/2001 | Mielke | B63B 19/18 114/343 |
| 2002/0083781 | A1 * | 7/2002 | Golner | G01N 1/14 73/863.83 |
| 2002/0112529 | A1 * | 8/2002 | Bondarowicz | G01N 33/2888 73/53.05 |
| 2006/0276120 | A1 * | 12/2006 | Cherry, Sr. | F24F 13/28 454/56 |
| 2007/0029007 | A1 * | 2/2007 | Hutchinson | G01N 1/10 141/330 |
| 2007/0180934 | A1 | 8/2007 | Morris | |
| 2009/0038524 | A1 * | 2/2009 | Linares | B63B 19/18 114/202 |
| 2010/0327575 | A1 * | 12/2010 | Blanchard | F16L 37/32 285/34 |
| 2011/0023444 | A1 * | 2/2011 | Veilleux, Jr. | F02C 9/50 60/39.08 |
| 2011/0174250 | A1 * | 7/2011 | Borde | F01M 5/025 123/90.12 |
| 2011/0283817 | A1 * | 11/2011 | Decker | F16K 39/024 73/863.86 |
| 2012/0080384 | A1 | 4/2012 | Reinosa | |
| 2012/0118051 | A1 * | 5/2012 | Raadnui | G01N 15/0272 73/61.71 |
| 2012/0210769 | A1 * | 8/2012 | Roper | G01N 33/2847 73/23.31 |
| 2013/0197830 | A1 * | 8/2013 | Dvorak | G06Q 10/20 702/46 |
| 2014/0041463 | A1 * | 2/2014 | Vethe | E21B 41/04 73/863.51 |
| 2014/0121994 | A1 * | 5/2014 | Jean | G01N 31/22 702/27 |
| 2015/0308304 | A1 | 10/2015 | Apostolides et al. | |
| 2016/0370341 | A1 * | 12/2016 | Jean | H01J 37/28 |
| 2017/0159485 | A1 | 6/2017 | Jean et al. | |
| 2017/0336380 | A1 * | 11/2017 | McKeague | E03B 7/07 |
| 2018/0340896 | A1 * | 11/2018 | Briden | G01T 3/001 |
| 2019/0076683 | A1 * | 3/2019 | McHugh, IV | A62C 35/62 |
| 2019/0126006 | A1 * | 5/2019 | Rehm | A61F 5/44 |
| 2019/0234860 | A1 | 8/2019 | Jean et al. | |
| 2020/0231421 | A1 * | 7/2020 | Singh | B67D 1/0004 |

OTHER PUBLICATIONS

Anonymous, Filtration Approved by the US Patent Office—A major innovation in bypass filtration and the first to deploy parallel-flow technology, Nov. 12, 2014, San Pedro, USA.

Wikipedia, Quick connect fitting, accessed on Aug. 2, 2019 from en.wikipedia.org/wiki/Quick_connect_fitting.

* cited by examiner

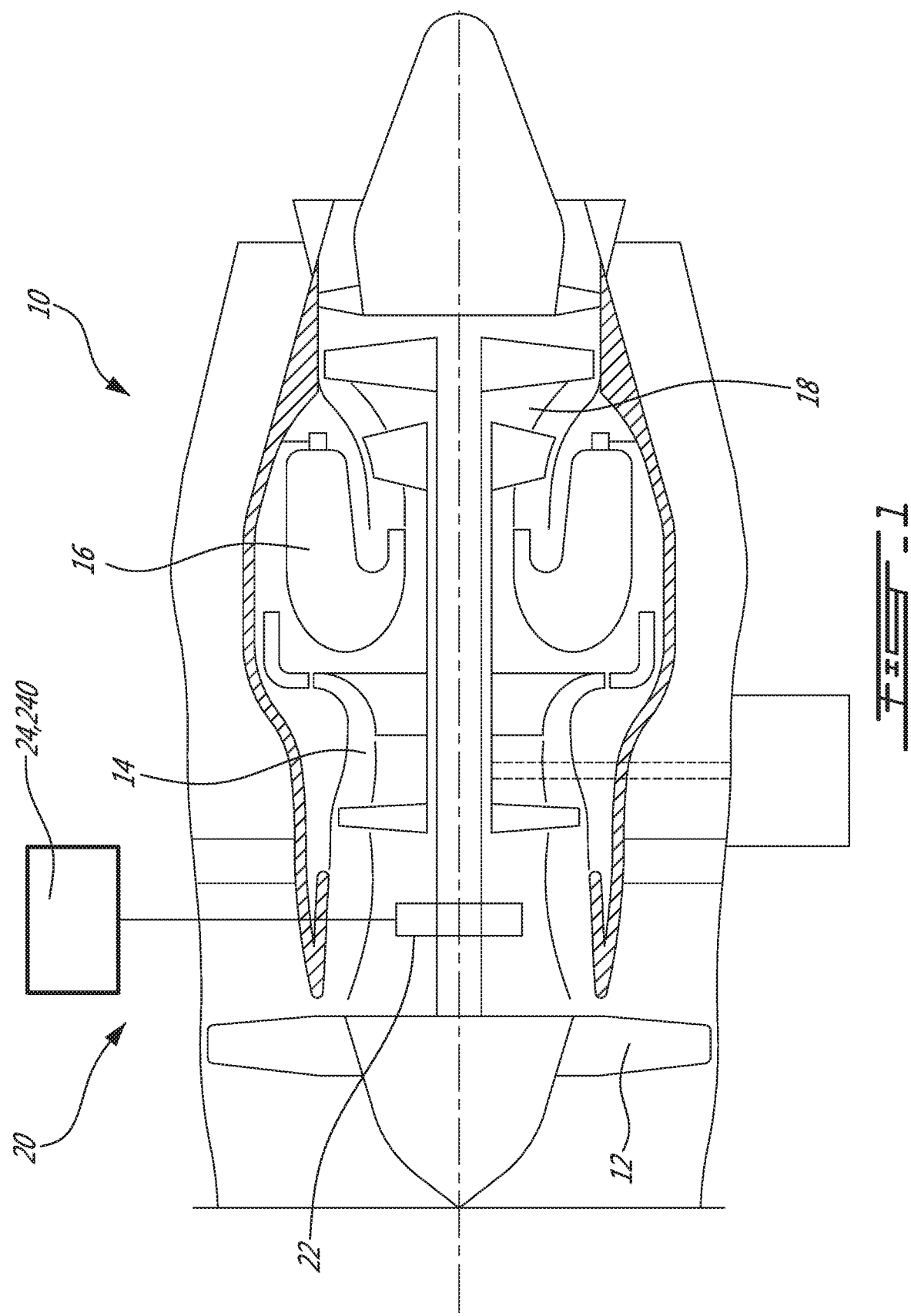

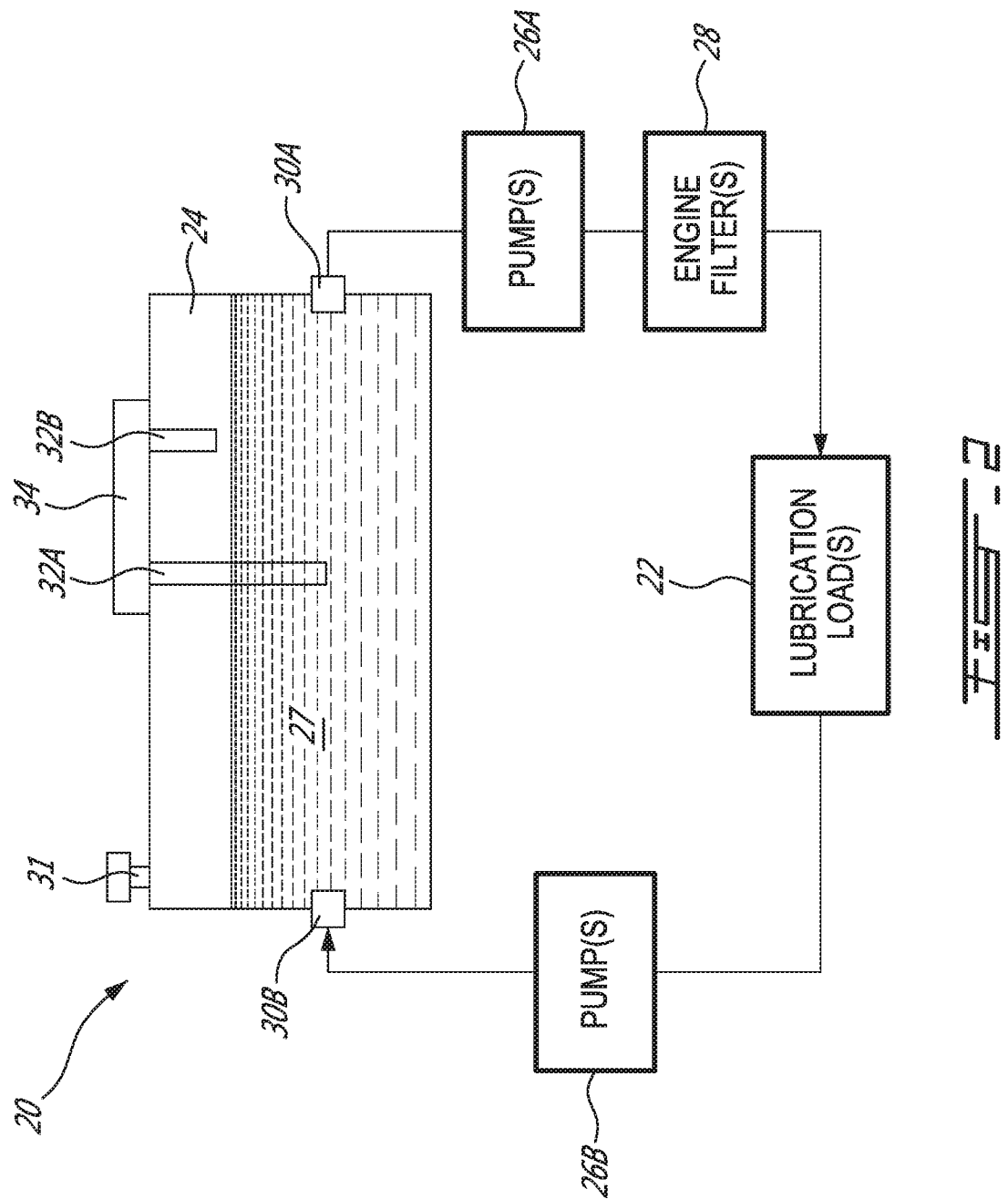

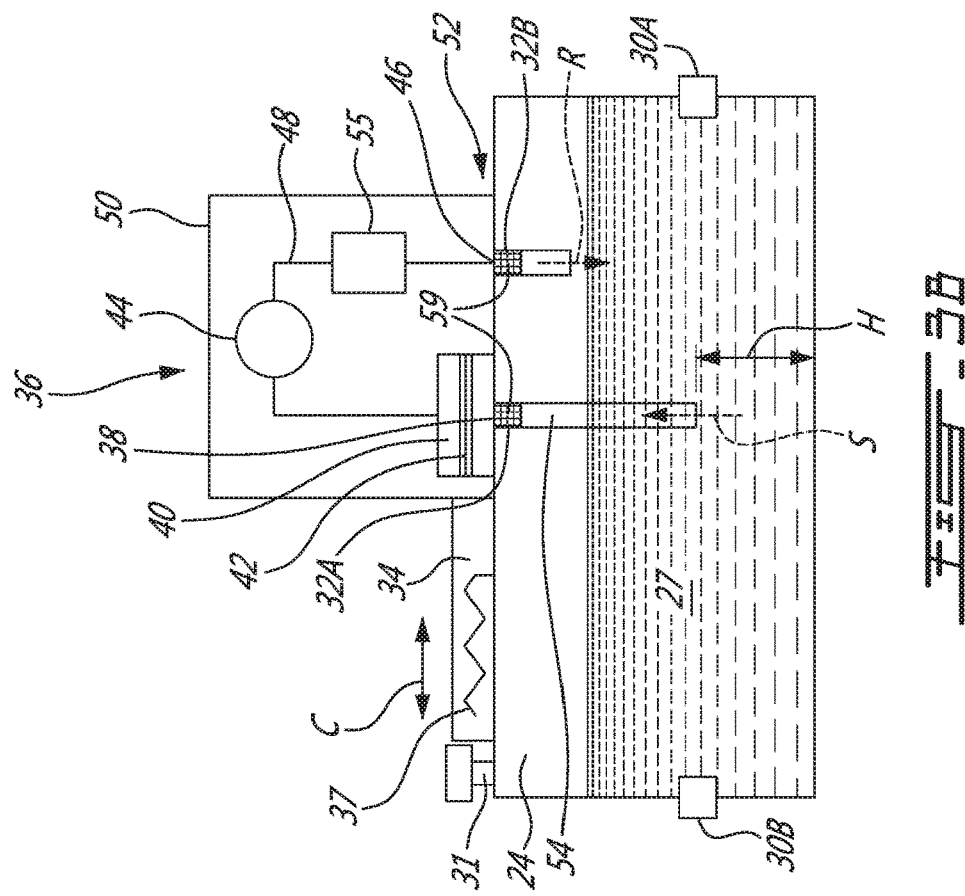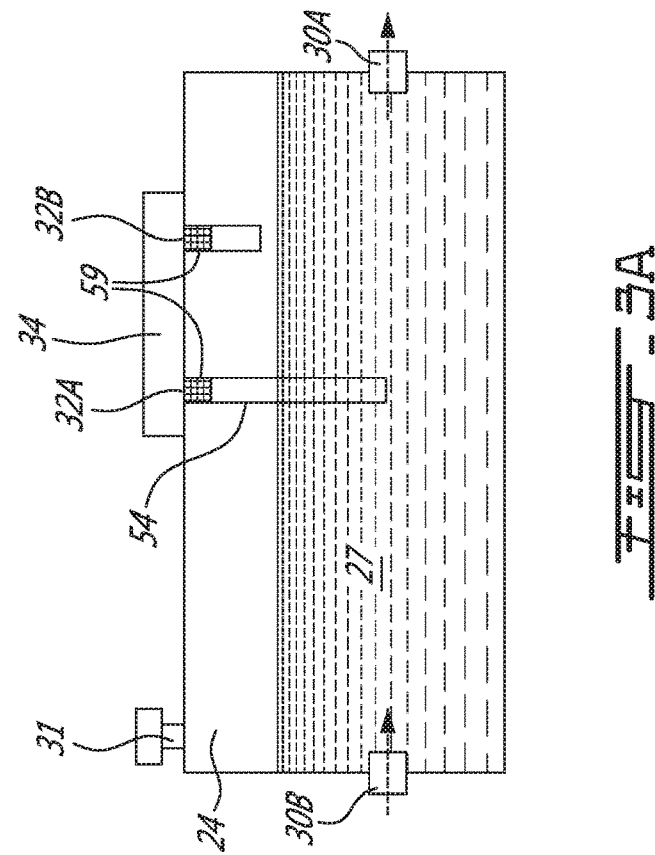

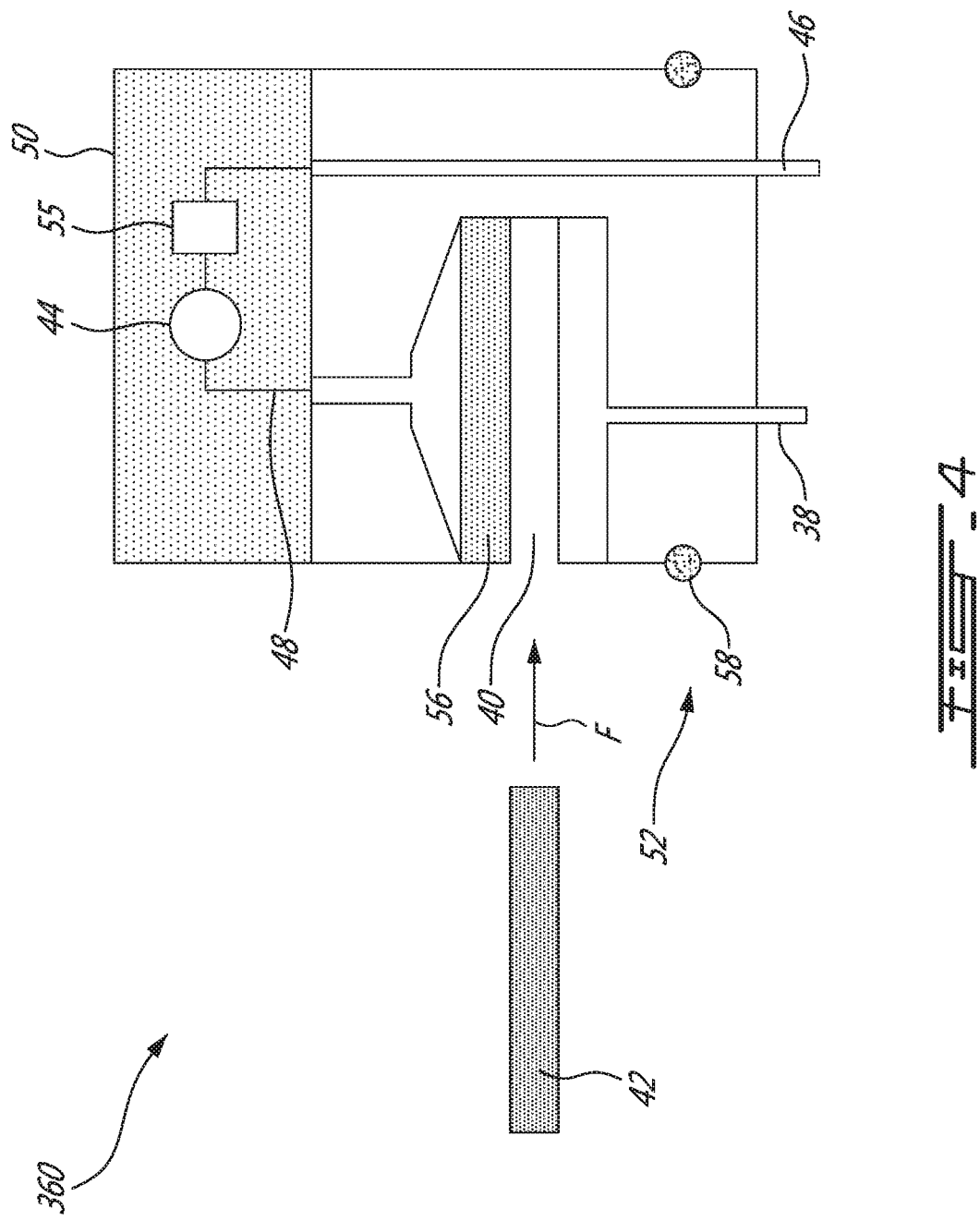

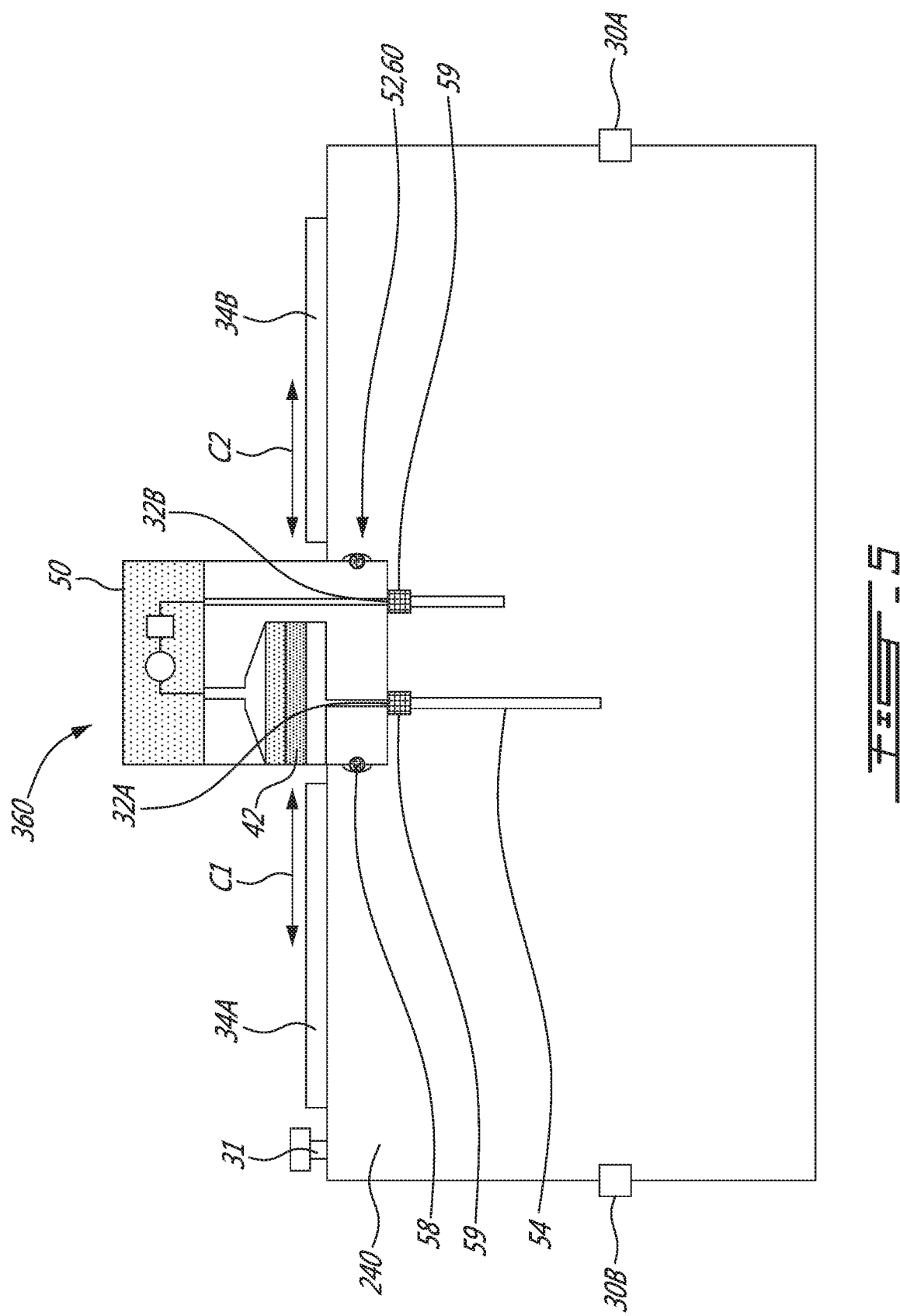

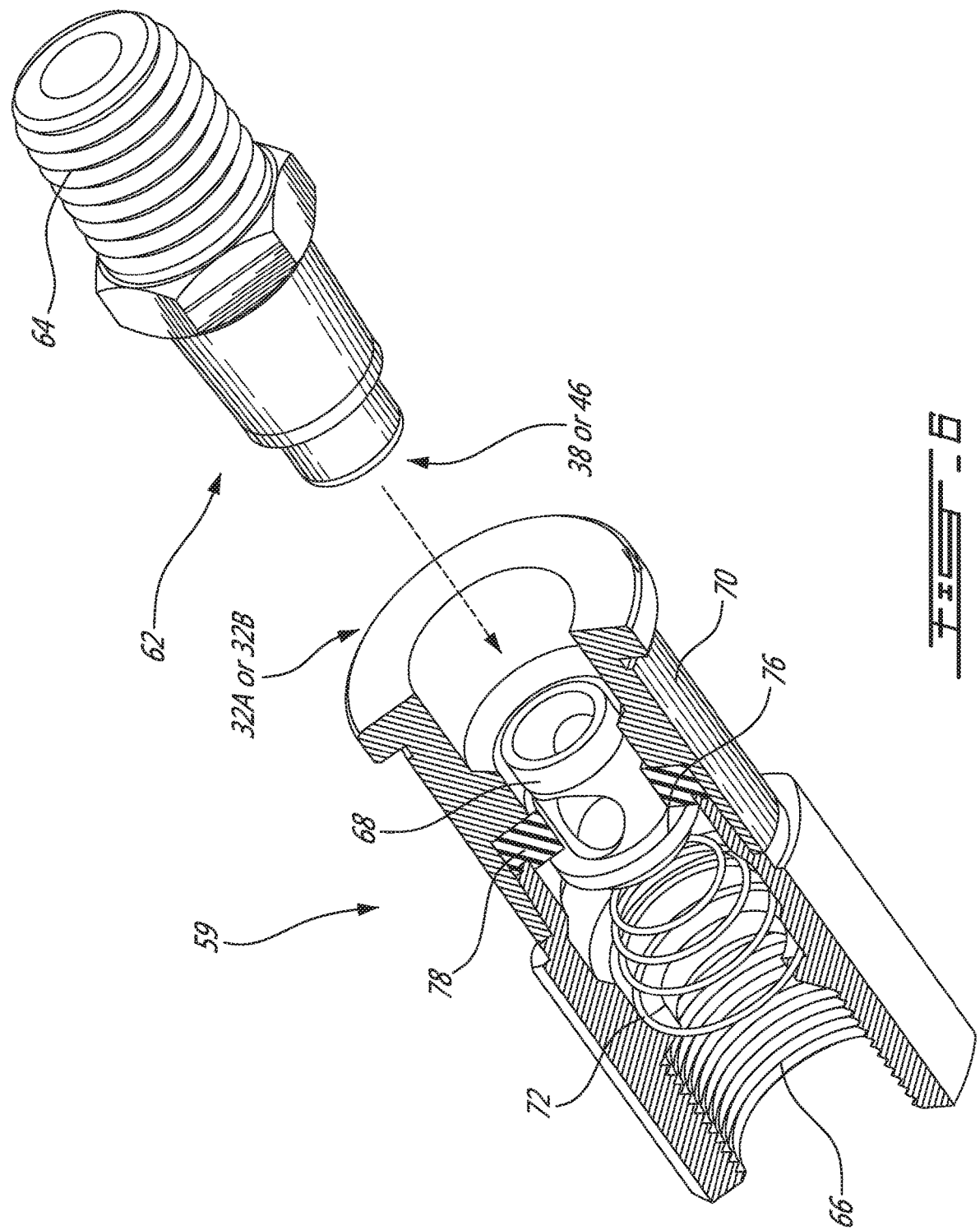

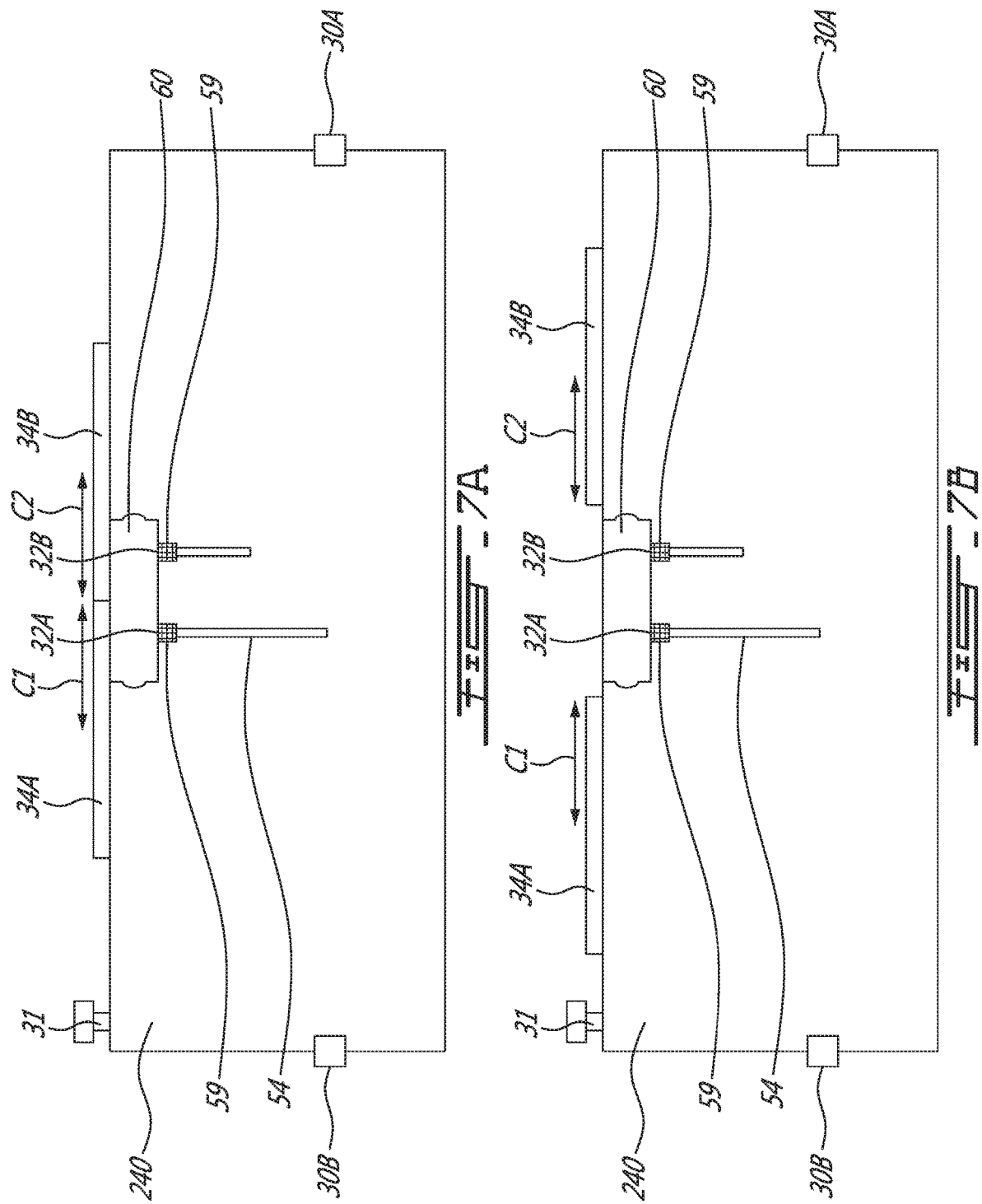

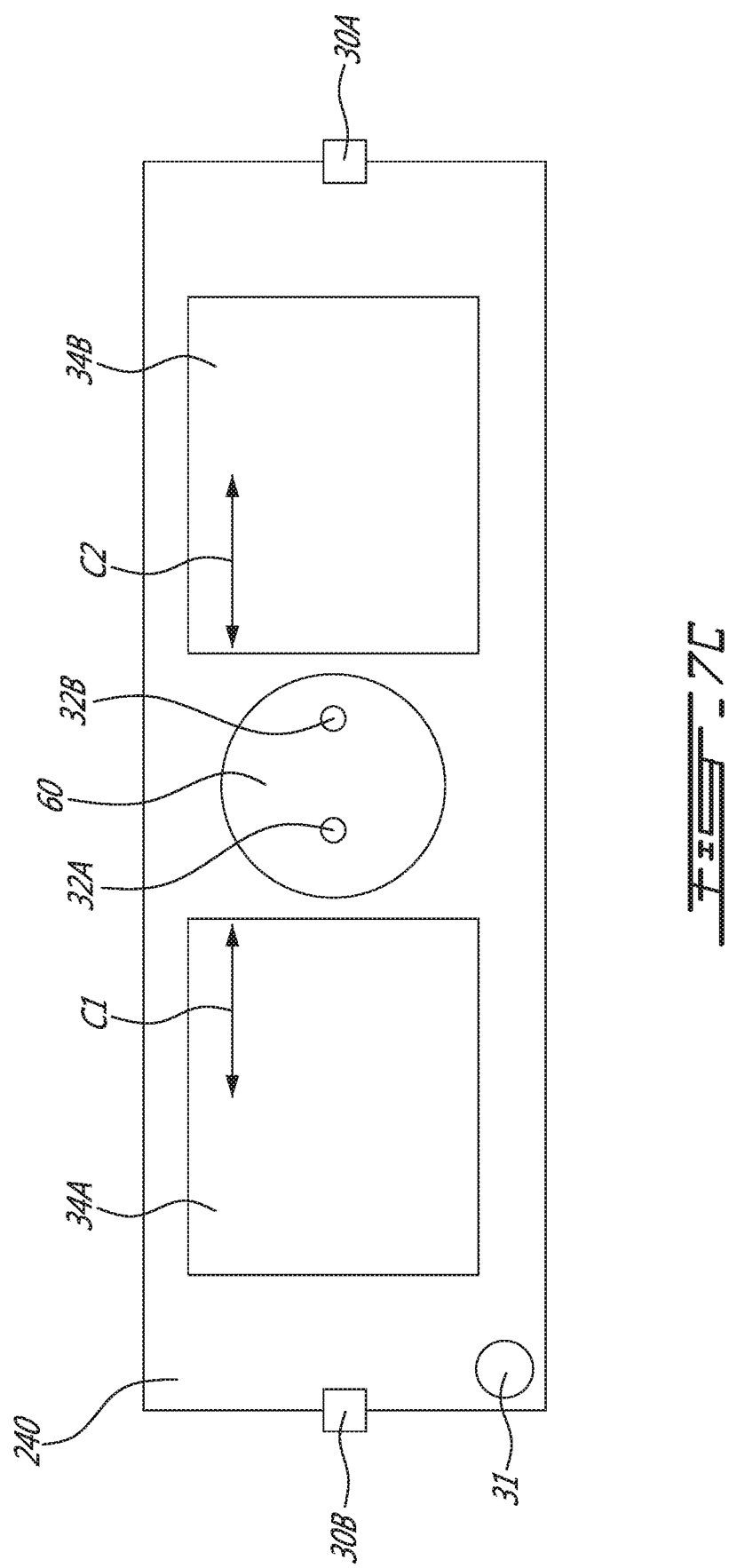

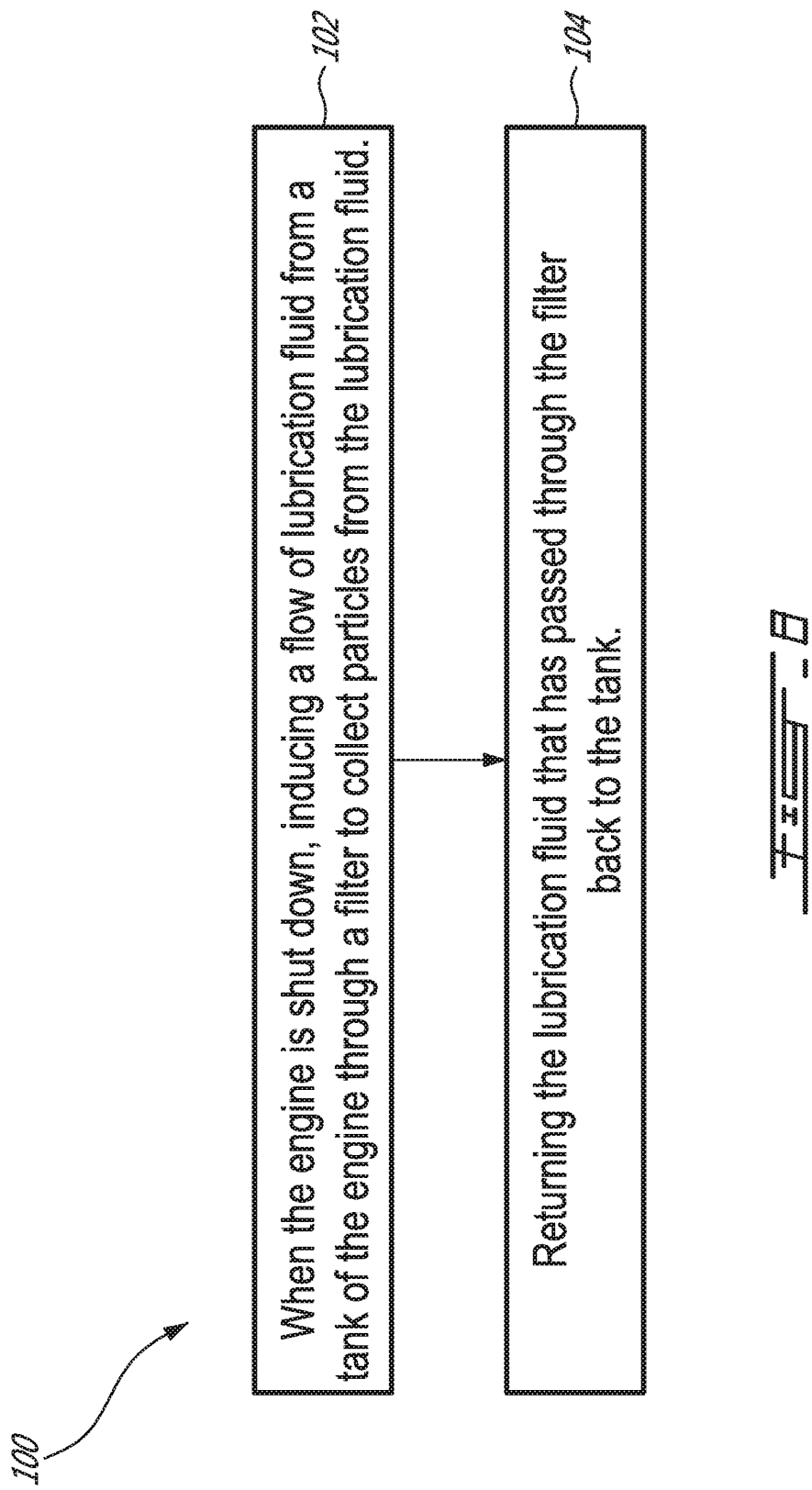

SAMPLING TOOL FOR LUBRICATING FLUID ANALYSIS

TECHNICAL FIELD

The disclosure relates generally to engines, and more particularly to tools for collecting samples for diagnosing engine conditions using lubricating fluid analysis.

BACKGROUND

Engine oil analysis can be used for identifying premature wear of engine components. One approach for monitoring engine wear is to perform an analysis on particles extracted from the engine filter. This method is relatively costly because the engine filter must be removed to extract the particles and is typically not reused. Removing the engine filter may be time consuming. Accordingly, such filter analysis typically is not performed frequently and is mainly used to monitor engines already identified as potentially behaving abnormally. Such filter analysis is also limited to a range of particle sizes that are captured by the filter.

Another method for monitoring engine wear is to perform an analysis on particles collected from the oil by a magnetic drain plug. However, this method is limited to only particles that are captured by the magnetic plug.

SUMMARY

In one aspect, the disclosure describes an oil sampling assembly for an aircraft engine. The oil sampling assembly comprises:
a tank of the aircraft engine, the tank containing lubrication fluid of the engine, the tank including a port and a self-closing valve configurable between a closed configuration where a flow of lubrication fluid through the port is prevented and an open configuration where the flow of lubrication fluid through the port is permitted; and
an oil sampling tool releasably engaged with the self-closing valve to cause opening of the self-closing valve, the sampling tool having:
an inlet in fluid communication with the port for receiving the flow of lubrication fluid from the tank via the port;
a filter in fluid communication with the inlet; and
a pump configured to induce the flow of the lubrication fluid through the filter.

In another aspect, the disclosure describes an assembly comprising:
an engine having a tank containing lubrication fluid of the engine, the tank including a supply port for supplying the lubrication fluid to a lubrication load of the engine, and a sampling port; and
a sampling tool configured to collect particles from the lubrication fluid contained in the tank, the sampling tool including:
an inlet in fluid communication with the sampling port for receiving the lubrication fluid from the tank;
a filter in fluid communication with the inlet; and
a pump configured to induce a flow of the lubrication fluid through the filter.

In a further aspect, the disclosure describes a method for collecting particles from lubrication fluid of an engine. The method comprises:

when the engine is shut down, inducing a flow of lubrication fluid from a tank of the engine through a filter to collect particles from the lubrication fluid; and
returning the lubrication fluid that has passed through the filter back to the tank.

Further details of these and other aspects of the subject matter of this application will be apparent from the detailed description included below and the drawings.

DESCRIPTION OF THE DRAWINGS

Reference is now made to the accompanying drawings, in which:

FIG. 1 is a schematic axial cross-section view of a turbo-fan gas turbine engine having a lubrication system as disclosed herein;

FIG. 2 is a schematic representation of an exemplary lubrication system of the engine of FIG. 1;

FIG. 3A is a schematic side elevation view of an exemplary tank of the lubrication system of FIG. 2;

FIG. 3B is a schematic side elevation view of the tank of FIG. 3A with an exemplary sampling tool detachably connected thereto;

FIG. 4 is a schematic representation of another exemplary sampling tool;

FIG. 5 is a schematic side elevation view of another exemplary tank of the lubrication system of FIG. 2 with the sampling tool of FIG. 4 detachably connected thereto;

FIG. 6 shows an exemplary self-closing valve of the tank of FIG. 5 with a cooperating connector of the sampling tool;

FIG. 7A is a schematic side elevation view of the tank of FIG. 5 with cover pieces in a covered position;

FIG. 7B is a schematic side elevation view of the tank of FIG. 5 with the cover pieces in an uncovered position;

FIG. 7C is a schematic top view of the tank of FIG. 5 with the cover pieces in the uncovered position; and FIG. 8 is a flow diagram of a method for collecting particles from lubrication fluid of an engine.

DETAILED DESCRIPTION

The sampling tool and method disclosed herein may be used to collect samples of particles filtered from lubrication fluid (lubricant) of gas turbine engines or other types of engines for the purpose of conducting analysis on such samples. Such analysis may be used to diagnose a condition of an engine. For example, the tool and method disclosed herein may be used in conjunction with lubrication fluid analysis methods such as those disclosed in U.S. Pat. No. 9,897,582 B2 entitled METHOD AND SYSTEM FOR FAILURE PREDICTION USING LUBRICATION FLUID ANALYSIS, and in U.S. Patent Publication No. 2017/0159485 A1 entitled METHOD AND SYSTEM FOR DIAGNOSING A CONDITION OF AN ENGINE USING LUBRICATION FLUID ANALYSIS, both of which being incorporated herein by reference.

Aspects of various embodiments are described through reference to the drawings.

FIG. 1 is a schematic axial cross-section view of gas turbine engine 10 of a (e.g., turbo-fan) type preferably provided for use in subsonic flight, generally comprising in serial flow communication fan 12 through which ambient air is propelled, multistage compressor 14 for pressurizing the air, combustor 16 in which the compressed air is mixed with fuel and ignited for generating an annular stream of hot combustion gases, and turbine section 18 for extracting energy from the combustion gases. Engine 10 may be mounted to an aircraft and used to propel such aircraft. Engine 10 may include lubrication system 20 shown schematically in FIG. 1. Lubrication system 20 may serve to lubricate, cool and clean one or more lubrication loads 22 such as bearings and gears of engine 10.

FIG. 2 is an exemplary schematic representation of lubrication system 20 that may be part of engine 10. Lubrication system 20 may include tank 24 and other components such as one or more pumps 26A, 26B, one or more valves (not shown), and one or more engine filters 28. Tank 24 may be a reservoir containing a supply of lubrication fluid 27 such as oil for use by lubrication system 20. Pump 26A may be a pressure pump for driving lubrication fluid 27 toward lubrication load(s) 22. Pump 26B may be a scavenge pump for returning lubrication fluid 27 from sumps and bearing cavities back to tank 24. Tank 24 may have one or more system supply ports 30A for supplying lubrication fluid 27 to lubrication load(s) 22, and one or more system return ports 30B for returning lubrication fluid 27 from lubrication load(s) 22 back to tank 24. Tank 24 may have fill port 31 for adding lubrication fluid 27 to tank 24. Fill port 31 may be made accessible by the removal of a fill cap that is intended to be installed to and secure fill port 31 during operation of engine 10.

Tank 24 may also have sampling port 32A and return port 32B that may be used with a sampling tool as disclosed herein. In some embodiments, sampling port 32A and return port 32B may be separate (i.e., different) from system supply and return ports 30A, 30B of tank 24. For example, sampling port 32A and return port 32B may be dedicated for use with the sampling tool and otherwise not used during the operation of engine 10. In other words, sampling port 32A and return port 32B may not be used to supply lubrication load(s) 22 with lubrication fluid 27 during operation of engine 10. Accordingly, sampling port 32A and return port 32B may be covered by one or more covers 34 so as to be secured and unavailable during operation of engine 10. In some embodiments, sampling port 32A and return port 32B may be separate (i.e., different) from fill port 31 of tank 24.

FIGS. 3A and 3B are schematic side elevation views of tank 24 of lubrication system 20. FIG. 3A shows tank 24 in an in-use configuration during operation of engine 10 where lubrication fluid 27 may be supplied to lubrication load(s) 22 via system supply port 30A and returned back to tank 24 via system return port 30B. In the in-use configuration, cover 34 is in the covered position where sampling ports 32A, 32B are covered and not used.

FIG. 3B shows tank 24 in a sampling configuration when engine 10 may be shut down. In the sampling configuration, cover 34 may be moved to an uncovered position where sampling port 32A and return port 32B may be uncovered and available for interfacing with sampling tool 36. In some embodiments, cover 34 may be movable (e.g., slidable) between the covered and the uncovered positions along arrow C. For example, cover 34 may be slidably engaged with a (e.g., top) wall of tank 24 via one or more suitable slides or tracks (not shown). In some embodiments, cover 34 may be resiliently biased toward the covered position (e.g., toward the right in FIG. 3B), via one or more springs 37 for example, so that cover 34 may be manually pushed toward the uncovered position against the closing force exerted by spring 37 and held in the uncovered position to permit interfacing of sampling tool 36 with tank 24. Once sampling tool 36 is detachably connected to tank 24 as shown in FIG. 3B, the presence of sampling tool 36 may block the movement of cover 34 toward the covered position and hence hold cover 34 in the uncovered position.

Sampling tool 36 may be used to collect particles from lubrication fluid 27 of engine 10. Sampling tool 36 may be used when engine 10 is shut down. Sampling tool 36 may be external to (i.e., not part of) lubrication system 20 (shown in FIG. 2) of engine 10 but may be detachably connected to one or more components of lubrication system 20 during sampling. In some embodiments, sampling tool 36 may be a handheld and/or portable apparatus or unit that may be detachably connectable to lubrication system 20. Accordingly, sampling tool 36 may not be required for the normal operation of lubrication system 20 and of engine 10.

Sampling tool 36 may have inlet 38 for receiving lubrication fluid 27 from tank 24, filter-receiving portion 40 for receiving filter 42, and pump 44 configured to induce a flow of lubrication fluid 27 through filter 42 disposed in filter-receiving portion 40. Filter-receiving portion 40 may be in fluid communication with inlet 38. Sampling tool 36 may include outlet 46 for returning lubrication fluid 27 to tank 24 after lubrication fluid 27 has passed through filter 42. Fluid passage 48 may establish fluid communication between inlet 38 and outlet 46 of sampling tool 36. Fluid passage 48 may define a flow loop that is external to lubrication system 20 of engine 10 so that filter 42 is not disposed in-line within a flow circuit of lubrication system 20.

Sampling tool 36 may include housing 50 which may house pump 44 and optionally other components of sampling tool 36. In some embodiments, housing 50 may include interfacing portion 52 for detachable connection with tank 24. In some embodiments, interfacing portion 52 may be configured to provide one or more sealed connections between sampling tool 36 and tank 24. In some embodiments, a substantially liquid-sealed connection may be provided between inlet 38 and sampling port 32A via a suitable O-ring or other seal. The term "substantially" as used herein may be applied to modify any quantitative representation which could permissibly vary without resulting in a change in the basic function to which it is related.

Pump 44 may be disposed downstream of inlet 38. Pump 44 may be disposed downstream of filter-receiving portion 40. Pump 44 may be of a type suitable to generate a partial vacuum condition upstream thereof in order to draw lubrication fluid 27 from tank 24 into inlet 38 of sampling tool 36. In some embodiments, pump 44 may be a velocity pump such as a radial-flow pump or an axial-flow pump for example. Pump 44 may be configured to drive lubrication fluid 27 toward outlet 46. Pump 44 may be operatively disposed along fluid passage 48 between inlet 38 and outlet 46. Pump 44 may be electrically powered and may be driven using a power source that is external to engine 10. Alternatively, pump 44 may be manually powered and driven by an operator of sampling tool 36.

In some embodiments, tank 24 may include tube 54 through which lubrication fluid 27 is drawn (see arrow "S") and delivered to inlet 38 via sampling port 32A. Tube 54 may extend into the interior of tank 24 so that lubrication fluid 27 may be drawn at a desired height H from a bottom of tank 24 to avoid collecting particles that have settled to the bottom of tank 24 for example. Height H may also be selected to be at some depth below the surface of lubrication fluid 27 in order to collect particles that remain suspended in lubrication fluid 27 for some time after shutting down engine 10. Height H may be selected based on the type of engine 10 and also based on the type (e.g., size, composition, morphology and/or density) of particles that are of interest for the lubrication fluid analysis. In some embodiments, tube 54 may be permanently installed in tank 24 and may be part of tank 24. Alternatively, tube 54 may be part of sampling tool 36 and may extend into tank 24 through sampling port 32A.

Filter-receiving portion 40 may be a receptacle for holding one or more filters 42 in series with fluid passage 48. Filter 42 may include a screen, mesh or fabric (cloth) or a combination thereof. In some embodiments, filter 42 may be configured to capture relatively fine particles that would not be captured by engine filter 28 (shown in FIG. 2). In some embodiments, filter 42 may be a very fine filter, such as a 0.22 µm filter that is able to filter out even very small particles (e.g., as small as 0.5 µm in diameter or smaller). In some embodiments, filter 42 may be configured to collect particles that range in size from about 0.5 µm to about 1600 µm, for example. The type of filter 42 may be selected based on the type of particles that are of interest. In some embodiments, filter 42 may be a membrane filter. For example, filter 42 may be a membrane filter disposed inside a suitable holder (e.g., cartridge) for installation in filter-receiving portion 40.

In some embodiments, sampling tool 36 may have flowmeter 55 that is configured to measure the flow of lubrication fluid 27 induced by pump 44. In some embodiments, flowmeter 55 may be configured to measure a current flowrate of lubrication fluid 27 through fluid passage 48. In some embodiments, flowmeter 55 may be configured to measure and indicate a cumulative volume of lubrication fluid 27 being induced by pump 44. Flowmeter 55 may provide a useful indication that allows an operator of sampling tool 36 to control the operation of pump 44 in order to cause only a prescribed amount (e.g., volume) of lubrication fluid to pass through filter 42 for controlled and repeatable sample collection. In some embodiments, the timely deactivation of pump 44 may be achieved manually by an operator based on an indication from flowmeter 55. In some embodiments, the timely deactivation of pump 44 may be achieved automatically by way of a trigger signal generated by flowmeter 55 once the prescribed amount of lubrication fluid 27 has passed through filter 42.

In some embodiments, sampling tool 36 may be devoid of any reservoir for collecting a sample of lubrication fluid 27. Accordingly, most or substantially all of lubrication fluid 27 that is drawn into inlet 38 may be returned to tank 24 via outlet 46. Filter 42 with the particles captured therein may be sent to a suitable testing facility to perform the desired analysis and diagnose a condition of engine 10. Accordingly, returning lubrication fluid 27 back to tank 24 through the use of sampling tool 36 may significantly reduce wastage of lubrication fluid 27 especially when samples are collected at regular intervals on several engines 10. Returning lubrication fluid 27 back to tank 24 may also reduced shipping costs by reducing the size and weight of the samples that are shipped to the testing facility.

In some embodiments, tank 24 may include one or more optional self-closing valves 59 (described in more detail below in reference to FIG. 6) associated with sampling port 32A and/or return port 32B. Self-closing valves 59 may be configurable between a closed configuration where a flow of lubrication fluid 27 through sampling port 32A and/or return port 32B is prevented and an open configuration where the flow of lubrication fluid 27 through sampling port 32A and/or return port 32B is permitted. During use of sampling tool 36, inlet 38 or other part(s) of sampling tool 36 may be releasably engaged with self-closing valve 59 associated with sampling port 32A to cause opening of self-closing valve 59. Similarly, during use of sampling tool 36, outlet 46 or other part(s) of sampling tool 36 may be releasably engaged with self-closing valve 59 associated with return port 32B to cause opening of self-closing valve 59. Self-closing valve(s) 59 may be configured to be in the open configuration when sampling tool 36 is being used, and automatically return to the closed configuration when sampling tool 36 is disconnected from tank 24 and not being used.

The use of dedicated sampling port 32A and return port 32B with associated optional self-closing valves 59 may reduce safety risks associated with the use of sampling tool 36. For example, since sampling and return ports 32A and 32B are different from fill port 31, the removal of a fill cap associated with fill port 31 may not be required to use sampling tool 36. Accordingly, the risk of leakage or contamination of lubrication fluid 27 due to fill cap being inadvertently left uninstalled after the use of sampling tool 36 and during operation of engine 10 may be reduced. Also, the use of self-closing valves 59 may automatically cause closing of sampling and return ports 32A, 32B when sampling tool 36 is disconnected from tank 24 so that the risk of leakage or contamination of lubrication fluid 27 due to such ports 32A, 32B being left open during operation of engine 10 is also reduced or eliminated.

FIG. 4 is a schematic representation of another exemplary sampling tool 360. Tool 360 may have components in common with tool 36 described above and like elements have been identified using like reference numerals. FIG. 4 shows filter 42 removed from tool 360 and indicates an insertion direction (see arrow F) for inserting filter 42 into tool 360. As explained below, filter 42 may be disposed inside a suitable cartridge that is permeable to lubrication fluid 27 and that allows filter 42 to be removably retained in filter-receiving portion 40 of tool 360. Tool 360 may include an optional piece of porous glass 56 disposed downstream of filter 42 and through which lubrication fluid 27 is also induced to pass. Porous glass 56 may be a glass filter disc.

In some embodiments, housing 50 of tool 360 may house pump 44, flowmeter 55 filter-receiving portion 40. Interfacing portion 52 of housing 50 may be detachably connectable with lubrication system 20. In some embodiments, interfacing portion 52 of housing 50 may include seal 58 which may be an O-ring or other type of seal to provide a fluid-sealed interface between tool 360 and lubrication system 20 of engine 10.

FIG. 5 is a schematic side elevation view of another exemplary tank 240 of lubrication system 20 of engine 10 with sampling tool 360 detachably connected thereto, Tank 240 may include receptacle 60 formed in a upper wall of tank 240 for example. Receptacle 60 may have a shape that is complementary to the shape of interfacing portion 52 of housing 50 so that interfacing portion 52 of housing 50 may be received in receptacle 60 when tool 360 is detachably connected to tank 240. Seal 58 may be disposed between interfacing portion 52 of housing 50 and one or more walls of receptacle 60. Seal 58 may provide a sealed interface between housing 50 and tank 240. It is understood that a separate substantially sealed interface may be provided between inlet 38 of tool 360 and sampling port 32A.

Tank 240 may include a two-piece cover 34 (e.g., pieces 34A, 34B) for covering receptacle 60 and sampling ports 32A, 32B during operation of engine 10. Cover pieces 34A, 34B may be movable in opposite directions along arrows C1 and C2 respectively to cause covering and uncovering of receptacle 60 and sampling ports 32A, 32B. In some embodiments, cover pieces 34A, 34B may be resiliently biased toward their respective covered positions in a same manner as cover 34 of tank 24 (see FIG. 3B) or in a different manner.

FIG. 6 shows an exemplary self-closing valve 59 of tank 24 with a cooperating connector 62 of sampling tool 36. One or more connectors 62 may be connected to part of sampling tool 36 via threaded interface 64. For example, one connector 62 may define inlet 38 and another connector 62 may define outlet 46 (see FIG. 3B). Connector 62 may have a through central passage for the flow of lubrication fluid 27 and in fluid communication with fluid passage 48 of sampling tool 36. Connector 62 may be configured to engage with self-closing valve 59 when sampling tool 36 is in use and can cause self-closing valve 59 to adopt the open configuration.

Self-closing valve 59 is shown in a partially sectioned and perspective view to illustrate internal components thereof. One or more self-closing valves 59 may be connected to part of tank 24 via threaded interface 66. For example, one self-closing valve 59 may define sampling port 32A and another self-closing valve 59 may define return port 32B (e.g., see FIG. 3B). Self-closing valve 59 may have a through central passage for the flow of lubrication fluid 27. Self-closing valve 59 may have valve member 68 movably disposed inside housing 70. Valve member 68 may be resiliently biased by spring 72 toward a valve-closed position that is shown in FIG. 6. In the valve-closed position, a sealing surface 76 (shoulder) may be in sealing contact with seal 78 in order to substantially prevent the flow of lubrication fluid 27 out of sampling port 32A and/or out of return port 32B.

When sampling tool 36 is brought in releasable engagement with tank 24 for the purpose of obtaining a sample of particles from lubrication fluid 27, connector 62 may be inserted into self-closing valve 59 and may push valve member 68 and cause movement of valve member 68 to a valve-open position where annular sealing surface 76 and annular seal 78 are no longer in contact and no longer provide sealing. The pushing of valve member 68 by connector 62 would overcome the closing force provided by spring 72. When sampling tool 36 is removed from tank 24 after a sampling procedure, the withdrawal of connector 62 from self-sealing valve 59 may allow valve member 68 to automatically return to its valve-closed position due to the closing force provided by spring 72.

The combination of connector 62 and self-sealing valve 59 may define a quick connect/release fitting between sampling tool 36 and tank 24. In some embodiments, self-sealing valve 59 may be a check valve that prevents fluid flow out of tank 24 except when self-sealing valve 59 is urged to a valve-open configuration by connector 62 for example. It is understood that self-closing valve 59 could be of other type than illustrated herein. For example, self-closing valve 59 could be a ball check valve, a diaphragm check valve, a swing check valve, a flapper valve or a lift check valve in various embodiments.

FIG. 7A is a schematic side elevation view of tank 240 with cover pieces 34A, 34B in their respective covered positions.

FIG. 7B is a schematic side elevation view of tank 240 with cover pieces 34A, 34B in their respective uncovered positions.

FIG. 7C is a schematic top view of tank 240 with cover pieces 34A, 34B in their respective uncovered positions. In some embodiments, receptacle 60 and interfacing portion 52 of housing 50 may each have a circular cross-section profile but it is understood that other shapes of cross-sectional profiles may also be suitable.

FIG. 8 is a flow diagram of method 100 for collecting particles from lubrication fluid 27 of engine 10. Method 100 may be performed using sampling tools 36 or 360, or may be performed using other suitable sampling tools. Accordingly, structural and functional aspects of tools 36, 360 disclosed above may also be incorporated into method 100. Method 100 may include:

when engine 10 is shut down, inducing a flow of lubrication fluid 27 from tank 24, 240 of engine 10 through filter 42 to collect particles from lubrication fluid 27 (see block 102); and returning lubrication fluid 27 that has passed through filter 42 back to tank 24, 240 (see block 104).

Method 100 may include inducing only a prescribed amount of lubrication fluid 27 through filter 42. Method 100 may include using pump 44 external to lubrication system 20 of engine 10 to induce the flow of lubrication fluid 27 from tank 24, 240. Filter 42 may be external to lubrication system 20 of engine 10.

The timing of the acquisition of the particles after shut down of engine 10 may also be prescribed based on particles of interest that are expected to still be suspended in lubrication fluid 27. For example, method 100 may be performed within a prescribed time window from the shut down of engine 10 in order to provide consistent and repeatable analysis.

The above description is meant to be exemplary only, and one skilled in the relevant arts will recognize that changes may be made to the embodiments described without departing from the scope of the invention disclosed. The present disclosure may be embodied in other specific forms without departing from the subject matter of the claims. The present disclosure is intended to cover and embrace all suitable changes in technology. Modifications which fall within the scope of the present invention will be apparent to those skilled in the art, in light of a review of this disclosure, and such modifications are intended to fall within the appended claims. Also, the scope of the claims should not be limited by the preferred embodiments set forth in the examples, but should be given the broadest interpretation consistent with the description as a whole.

What is claimed is:

1. An oil sampling assembly for an aircraft engine, the oil sampling assembly comprising:
    a tank of the aircraft engine, the tank containing lubrication fluid of the engine, the tank including a port and a self-closing valve configurable between a closed configuration where a flow of lubrication fluid through the port is prevented and an open configuration where the flow of lubrication fluid through the port is permitted; and
    an oil sampling tool releasably engaged with the self-closing valve to cause opening of the self-closing valve, the sampling tool having:
        an inlet in fluid communication with the port for receiving the flow of lubrication fluid from the tank via the port;
        a filter in fluid communication with the inlet;
        a pump configured to induce the flow of the lubrication fluid through the filter; and
        a housing, the pump being housed by the housing, a portion of the housing being received in a receptacle formed in the tank.

2. The oil sampling assembly as defined in claim 1, wherein:
    the port is a sampling port;
    the tank has a return port; and the oil sampling tool has an outlet in fluid communication with the return port for returning the lubrication fluid to the tank.

3. The oil sampling assembly as defined in claim 2, wherein:
the self-closing valve is a first self-closing valve; and
the tank includes a second self-closing valve associated with the return port.

4. The oil sampling assembly as defined in claim 2, wherein the pump is operatively disposed between the inlet and the outlet.

5. The oil sampling assembly as defined in claim 1, wherein the pump is disposed downstream of the filter.

6. The oil sampling assembly as defined in claim 1, wherein:
the oil sampling tool includes a connector defining the inlet; and
the connector is configured to engage with the self-closing valve to cause opening of the self-closing valve.

7. The oil sampling assembly as defined in claim 1, wherein the port is a sampling port that is different from a fill port of the tank and also different from a supply port for supplying the lubrication fluid to a lubrication load of the engine.

8. The oil sampling assembly as defined in claim 1, wherein the oil sampling tool is devoid of a reservoir for collecting a sample of the lubrication fluid.

9. The oil sampling assembly as defined in claim 1, comprising a flowmeter configured to measure the flow of lubrication fluid induced by the pump.

10. An assembly comprising:
an engine having a tank containing lubrication fluid of the engine, the tank including a supply port for supplying the lubrication fluid to a lubrication load of the engine, and a sampling port; and
a sampling tool configured to collect particles from the lubrication fluid contained in the tank, the sampling tool including:
an inlet in fluid communication with the sampling port for receiving the lubrication fluid from the tank;
a filter in fluid communication with the inlet;
a pump configured to induce a flow of the lubrication fluid through the filter; and
a housing, the pump being housed by the housing, a portion of the housing being received in a receptacle formed in the tank.

11. The assembly as defined in claim 10, wherein:
the tank has a return port; and
the sampling tool has an outlet in fluid communication with the return port for returning the lubrication fluid to the tank.

12. The assembly as defined in claim 10, comprising a cover for covering the sampling port during operation of the engine.

13. The assembly as defined in claim 12, wherein:
the cover is movable between a covered position where the sampling port is covered by the cover, and an uncovered position where the sampling port is uncovered; and
the cover is resiliently biased toward the covered position.

14. The assembly as defined in claim 10, comprising a seal disposed between the receptacle formed in the tank and the portion of the housing received in the receptacle.

15. The assembly as defined in claim 10, wherein the sampling port is different from a fill port of the tank.

16. A method for collecting particles from lubrication fluid of an engine, the method comprising:
when the engine is shut down, inducing a flow of lubrication fluid from a tank of the engine through a filter to collect particles from the lubrication fluid, the tank including a supply port for supplying the lubrication fluid from the tank to a lubrication load of the engine, the tank including a sampling port, the flow being induced from the tank via the sampling port with a pump housed by a housing, a portion of the housing being received in a receptacle formed in the tank; and
returning the lubrication fluid that has passed through the filter back to the tank.

17. The method as defined in claim 16, comprising inducing only a prescribed amount of the lubrication fluid through the filter.

18. The method as defined in claim 16, wherein the pump is external to a lubrication system of the engine.

19. The method as defined in claim 16, wherein the filter is external to a lubrication system of the engine.

* * * * *